US006224739B1

(12) United States Patent
Reetz et al.

(10) Patent No.: US 6,224,739 B1
(45) Date of Patent: May 1, 2001

(54) PROCESS FOR PREPARING SOLVENT-STABILIZED METAL COLLOIDS AND SUBSTRATE-IMMOBILIZED METAL CLUSTERS

(75) Inventors: Manfred T. Reetz; Gunther Lohmer, both of Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/230,411

(22) PCT Filed: Jul. 16, 1997

(86) PCT No.: PCT/EP97/03807

§ 371 Date: Jan. 25, 1999

§ 102(e) Date: Jan. 25, 1999

(87) PCT Pub. No.: WO98/04763

PCT Pub. Date: Feb. 5, 1998

(30) Foreign Application Priority Data

Jul. 30, 1996 (DE) ............................................... 196 30 581

(51) Int. Cl.[7] .............................. C25B 3/00; B01F 17/08; B01F 17/00

(52) U.S. Cl. ................................ 205/464; 516/33; 516/97
(58) Field of Search .......................... 516/33, 97; 205/464

(56) References Cited

U.S. PATENT DOCUMENTS

| 3,532,518 | * | 10/1970 | D'Ottavio ........................... 516/97 X |
| 4,877,647 | * | 10/1989 | Klabunde ........................... 516/33 X |
| 5,147,841 | * | 9/1992 | Wilcoxon ........................... 516/33 X |
| 5,160,452 | * | 11/1992 | Marutsuka et al. ..................... 516/33 |
| 5,620,584 | * | 4/1997 | Reetz et al. ....................... 205/464 X |
| 5,925,463 | * | 7/1999 | Reetz et al. ....................... 205/464 X |

FOREIGN PATENT DOCUMENTS 347114    12/1989  (EP) .
672765     9/1995  (EP) .

* cited by examiner

Primary Examiner—Donald R. Valentine
(74) Attorney, Agent, or Firm—Norris McLaughlin & Marcus

(57) ABSTRACT

Solvent-stabilized transition metal colloids are prepared either electrochemically by cathodically reducing metal salts in the presence of polar stabilizing solvents to form metal colloids, or the transition metal salts are reduced in polar solvents using an alcohol at elevated temperatures.

16 Claims, 4 Drawing Sheets

PROCESS FOR PREPARING SOLVENT-STABILIZED METAL COLLOIDS AND SUBSTRATE-IMMOBILIZED METAL CLUSTERS

This application is a 371 of PCT/EP97/03807 filed on Jul. 16, 1997.

BACKGROUND OF THE INVENTION

The present invention relates to two surprisingly simple processes for the size-selective preparation of soluble metal colloids and of metal clusters fixed to supports. The invention also includes the preparation of bimetallic colloids and bimetallic clusters fixed to supports. Nanostructured metal colloids or clusters, especially in a range of sizes of 1 to 10 nm, are known to be useful catalysts. It has further long been known that the reduction of transition metal salts results in insoluble metal powders unless the reduction is performed in the presence of stabilizers which wrap around the intermediary nanometer-sized metal clusters and protect them against undesirable agglomeration [G. Schmid, Clusters and Colloids, VCH, Weinheim, 1994; B. C. Gates, L. Guczi, H. Knözinger, Metal Clusters in Catalysis, Elsevier, Amsterdam, 1986]. The stabilizers which have become known as yet include special ligands, such as triarylphosphanes, polymers, such as polyvinylpyrrolidones, surfactants, such as long-chain tetraalkylammonium salts ($R_4N^+X^-$), and in some cases special solvents. The reductants required for the reduction of the metal salts include, e.g., hydrogen, hydrazine, formaldehyde and various boron hydrides [ref.: see above]. Recently, the first electrochemical methods for the preparation of tetraalkylammonium salt stabilized metal colloids and their fixing to supports have been described [M. T. Reetz, W.Helbig, J. Am. Chem. Soc. 116 (1994), 7491; M. T. Reetz, S. A. Quaiser, Angew.Chem. 107 (1995), 2461, Angew. Chem. Int. Ed. Engl. 34 (1995), 2240]. Thus, a metallic sacrificial anode (e.g., a Pd sheet) is used as the metal source. In the presence of the conducting salt $R_4N^+X^-$, the metal sheet dissolves through anodic dissolution, the generated metal salts migrating to the cathode where they are reduced again. The metal atoms aggregate into nanostructured metal colloids stabilized by the tetraalkylammonium salts. Alternatively, two inert electrodes may be used in the electrochemical method, a transition metal salt serving as the metal source, i.e., the metal salts are directly reduced electrochemically in the presence of $R_4N^+X^-$. An essential advantage of this method is the fact that the size of the nanostructured $R_4N^+X^-$ stabilized clusters can be varied in a well-aimed manner by adjusting the current density. This is important because the size of metal clusters is known to have a strong influence on its catalytic properties [G. Schmid, Clusters and Colloids, VCH, Weinheim, 1994]. Indeed, the control of the cluster size is considered the greatest challenge in this field [J. S. Bradley, in Clusters and Colloids (G. Schmid, ed.), VCH, Weinheim, 1994, p. 490].

The disadvantages of the above mentioned methods include: 1) the high costs of some reductants, or their, in part, difficult handling, as in the case of hydrogen which involves a danger of explosion and specific and expensive handling methods; 2) lack of size selectivity; 3) complicated separation of reductants or side-products; 4) impure products from partial incorporation of the reductants (e.g., hydrogen or boron); and/or 5) use of expensive stabilizers, such as phosphanes or tetraalkylammonium salts.

In addition to the chemical and electrochemical reduction of transition metal salts in the presence of the above mentioned stabilizers, some metal colloids can also be prepared using metal vaporization [S. C. Davis, K. J. Klabunde, Chem. Rev.82 (1982), 153; K. J. Klabunde, G. Cardenas-Trivino, in Active Metals: Preparation, Characterization, Applications (A. Fürstner, ed.), VCH, Weinheim, 1996, p. 237]. Thus, a transition metal is vaporized, and the metal vapor is introduced into a cold matrix consisting of a solvent. In some cases, especially when polar solvents such as tetrahydrofurane or acetone are used, the metal colloid solutions generated at low temperatures could be brought to room temperature without an undesirable agglomerization of the nanostructured metal clusters occurring. This is due to solvent stabilization. Some of the thus prepared solvent-stabilized metal colloids have been employed as catalysts in hydrogenations. Thus, this method circumvents the above mentioned drawbacks. However, metal vaporization is an expensive method because complicated devices and a high expenditure of energy are required. The size selectivity on a preparatory scale is also problematic.

If hydrogen is used in special solvents, such as propylene carbonate, for the reduction of Pd salts, as in the in-situ hydrogenation of fatty acids, then solvent-stabilized Pd clusters are involved as hydrogenation catalysts [A. Behr, H. Schmidke, Chem. Ing. Tech. 65 (1993) 568; A. Behr, N. D öring, S. Durowicz-Heil, B. Ellenberg, C. Kozik, C. Lohr, H. Schmidke, Fett Wiss. Technol. 95 (1993) 2]. Size selectivity is not possible, however.

Another method relates to the simple thermolysis of certain transition metal salts in methyl isobutyl ketone as the solvent and stabilizer. The thermolysis of Pd salts in this medium could be used as an example to show that this solvent stabilizes Pd clusters. However, the Pd clusters are relatively large, i.e., larger than 8 nm, and further, a control of the cluster size, i.e., size selectivity, is not possible [K. Esumi, T. Tano, K. Meguro, Langmuir 5 (1989), 268].

DETAILED DESCRIPTION OF THE INVENTION

Figure 1:
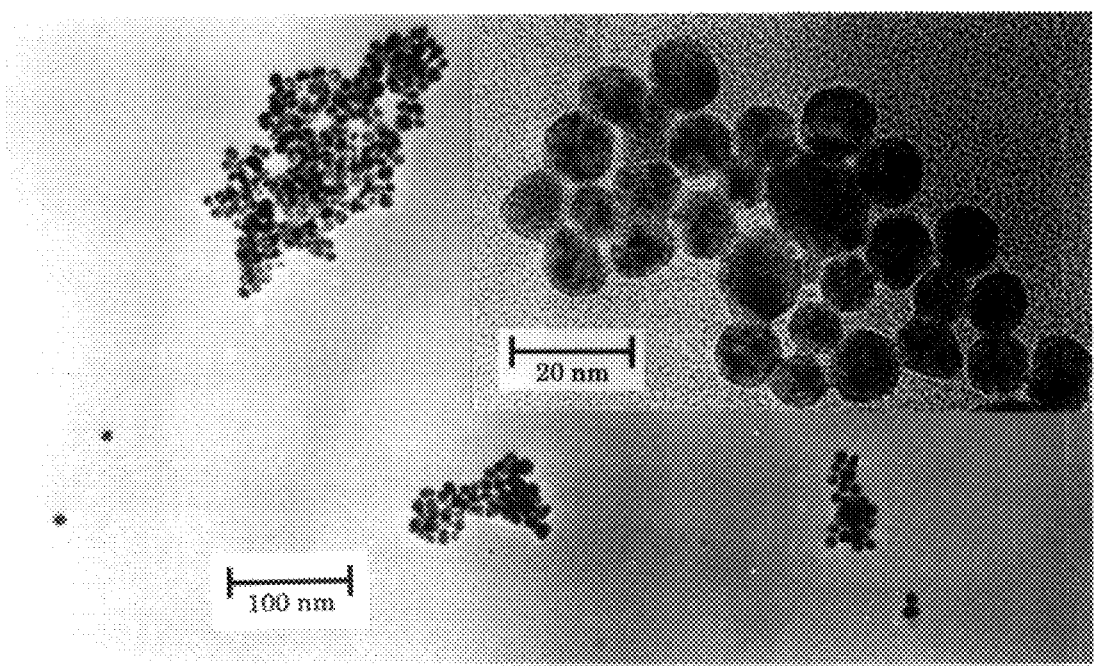
FIG. 1 is a HRTEM micrograph of the palladium colloid of Example 1 at a magnification of 100,000 (insert 500,000).

It has now been found that certain solvent-stabilized metal colloids are accessible either using electrochemical methods or by simple reduction of transition metal salts with alcohols in the presence of solvents capable of stabilizing metal colloids, and can be conveniently handled at room temperature and at even higher temperatures.

The metal colloids according to the invention do not require any surfactants or polymers for stabilization.

Two variants of the electrochemical method are possible, in principle. A sacrificial anode consisting of a metal, for example, can be used as the metal source. After the anodic dissolution, the metal salts released are reduced again at the cathode, the solvent serving as the stabilizer of the metal colloids or metal clusters (Scheme 1).

Scheme 1.

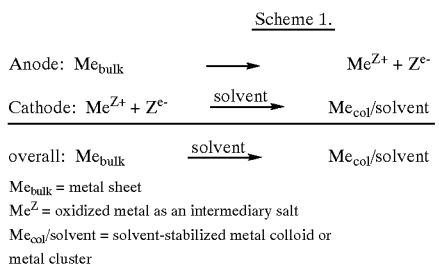

Me_bulk = metal sheet
Me^Z = oxidized metal as an intermediary salt
Me_col/solvent = solvent-stabilized metal colloid or metal cluster Alternatively, it is also possible to use transition metal salts as the metal source in the electrochemical preparation of solvent-stabilized metal colloids. In this case, an electrochemical apparatus consisting of two inert electrodes is used. Both variants include the use of solvents capable of stabilizing metal colloids or metal clusters, and a suitable conducting salt.

When metal sheets are employed as the metal source, transition metals such as Fe, Co, Ni, Pd, Cu, Ag or Au are used. When transition metal salts are used as the metal source, a wide variety of salts of transition metals are suitable, e.g., those of Fe, Co, Ni, Pd, Pt, Rh, Ru, Mo, Cu, Ag or Au. Polar solvents, such as organic carbonates (e.g., propylene carbonate), carboxylic acid amides (e.g., dimethylacetamide), sulfuric acid amides (e.g., $SO_2(NBu_2)_2$) or urea derivatives (e.g., tetrabutylurea), are used as the solvent and stabilizer. Propylene carbonate is preferably used. As the conducting salt, common inorganic salts, such as LiCl, NaCl, NaBr, $NaClO_4$, KCl or KBr, or organic salts, such as $(CH_3)_4N^+X^-$ or $(C_2H_5)_4N^+X^-$ (X=Cl, Br, I, OAc, $ClO_4$), which are themselves incapable of stabilizing clusters can be used. NaCl or $(CH_3)_4N^+X^-$ is preferably used as the conducting salt. The temperature in the electrolytic cell may be between −50° C. and +140° C., preferably from 25 to 70° C.

For controlling the size of the thus prepared metal clusters, parameters such as the current density can be varied (the higher the current density, the smaller the clusters), but the simplest method is through the choice of the conducting salt. While salts such as NaCl or KCl result in cluster sizes in the range of from 7 to 10 nm, the use of tetramethylammonium or tetraethylammonium salts results in cluster sizes of from 2 to 5 nm.

For the preparation of solvent-stabilized metal colloids or metal clusters by reduction with alcohols, transition metal salts are heated in a suitable solvent. The salt is thus converted to the metallic form which is generated in the form of soluble nanostructured metal colloids or metal clusters which are stabilized by the solvent. As in the case of the electrochemical methods, polar solvents, such as organic carbonates, carboxylic acid amides, sulfuric acid amides or urea derivatives, preferably propylene carbonate, are useful for the stabilization of the colloids or clusters. The preparation is performed by heating the solution or suspension of a transition metal salt in the presence of an alcohol in said solvent, i.e., in a range of from 30 to 130° C., preferably from 60 to 100° C.

Typical salts are $PdCl_2$, $Pd(OAc)_2$, $Pd(acac)_2$, $Ni(OAc)_2$, $Fe(acac)_2$, $Fe(OAc)_3$, $PtCl_2$, $Pt(OAc)_2$, $RhCl_3$, $Rh(OAc)_3$, $Co(OAc)_2$, $Cu(OAc)_2$, AgOAc or $Ag_2CO_3$. It is also possible to produce specific salts in situ, e.g., $Pt(OAc)_2$, by mixing $PtCl_2$ and NaOAc during the reduction. The nature of the alcohol employed for the reduction is critical to the size selectivity. Branched alcohols, such as isopropanol, result in small clusters, e.g., in a range of from 2 to 5 nm, whereas methanol yields larger clusters, typically in a range of from 6 to 10 nm.

The preparation of solvent-stabilized bimetallic colloids or clusters requires two metal sources. Three variants of the electrochemical method are possible: 1) two sacrificial anodes are used; 2) one sacrificial anode and one metal salt are used; 3) two different metal salts are used. For the reduction with alcohols, two different metal salts are dissolved or suspended in a suitable polar solvent in the presence of an alcohol, followed by heating.

For characterizing the metal colloids, the usual analytical methods are employed, especially transmission electron microscopy (TEM). The thermal stability of the colloidal solutions is examined by simple heating. If the formation of a metal powder is observed at a certain temperature, the colloid is unstable under such conditions.

The size of the colloids or clusters prepared according to the invention as determined by TEM studies is within the nanometer range in all cases, typically between 2 and 15 nm. Surprisingly, the size distribution of the metal clusters is uniform. As to thermal stability, many of the colloidal solutions prepared according to the invention are unusually stable. A typical example is an 0.1 M propylene carbonate solution of 8–10 nm sized Pd clusters which is stable at 160° C. for at least 3 days and exhibits no signs of the formation of a Pd powder. This is in contrast to conventionally stabilized metal clusters, such as $R_4N^{+K-}$ stabilized Pd colloids, which quickly decompose at 130–140° C. already. This unusually high thermal stability of the solvent-stabilized colloids is an unexpected property which is useful, in particular, for applications in catalysis.

The application of the colloidal solutions in catalysis may involve a wide variety of chemical reactions, such as hydrogenations, oxidations and C—C bond-forming reactions, such as Heck or Suzuki couplings.

The solvent-stabilized metal or bimetallic clusters herein described can also be fixed to supports. Thus, the colloidal solutions are treated with solid, optionally doped, supports, such as metaloxides (e.g., $SiO_2$, $Al_2O_3$ or $TiO_2$), active charcoal or polymers (e.g., polyaramides). After such mixtures have been stirred or agitated, the solid support is allowed to settle, the liquid is filtered or decanted, and the solid material is dried. If pellets are used as the support (e.g., $Al_2O_3$ pellets), shell catalysts are readily prepared.

Both the colloidal clusters and the support-fixed forms of the metal clusters are suitable as catalysts for a variety of different reactions, such as hydrogenations, oxidations and C—C bond-forming reactions. For example, propylene carbonate stabilized Pd clusters are suitable as catalysts in the Heck reaction of chloroaromatics at 130 to 160° C.

The advantages of the preparation and application of the solvent-stabilized metal colloids or metal clusters prepared according to the invention include:
1. simple preparation method;
2. inexpensive and non-polluting solvents or stabilizers;
3. simple controlling of the cluster size;
4. surprisingly uniform cluster sizes;
5. surprisingly high thermal stability of the colloidal solutions which allows to perform catalytic processes such as Heck reactions of poorly reactive chloroaromatics at higher temperatures;
6. simple fixing of the preformed clusters to supports, especially in the preparation of shell catalysts.

EXAMPLE 1

Preparation of propylene carbonate stabilized palladium colloid

Under argon, 50 ml of propylene carbonate, 5 ml of ethanol and 1 g of NaCl are electrolyzed between a palladium anode and a platinum cathode. The reaction is performed in an ultrasonic bath at a controlled temperature of 70° C. The electrolysis proceeds in a galvanostatic manner at a current density of 3 mA/cm$^2$. After a charge of 2002·10$^{-4}$ Ah has flown, the synthesis is completed, and the deep-brown colloidal solution is filtered over a glass filter frit. The product thus obtained contains palladium particles of between 8 and 10 nm in a narrow size distribution (FIG. 1).

EXAMPLE 2

Preparation of propylene carbonate stabilized palladium colloid

Under argon, 50 ml of propylene carbonate and 200 mg of tetramethylammonium bromide are electrolyzed between a palladium anode and a platinum cathode. The reaction is performed in an ultrasonic bath at a controlled temperature of 25° C. The electrolysis proceeds in a galvanostatic manner at a current density of 3 mA/cm$^2$. After a charge of 8598·10$^{-4}$ Ah has flown (anode weight loss: 1.1 g), the synthesis is completed, and the deep-brown colloidal solution is filtered over a glass filter frit. The product thus obtained contains palladium particles of between 4 and 6 nm. By adding diethyl ether, the colloid can be obtained as a slightly smearing solid which can be redispersed in propylene carbonate.

EXAMPLE 3

Preparation of propylene carbonate stabilized platinum colloid

Figure 2:
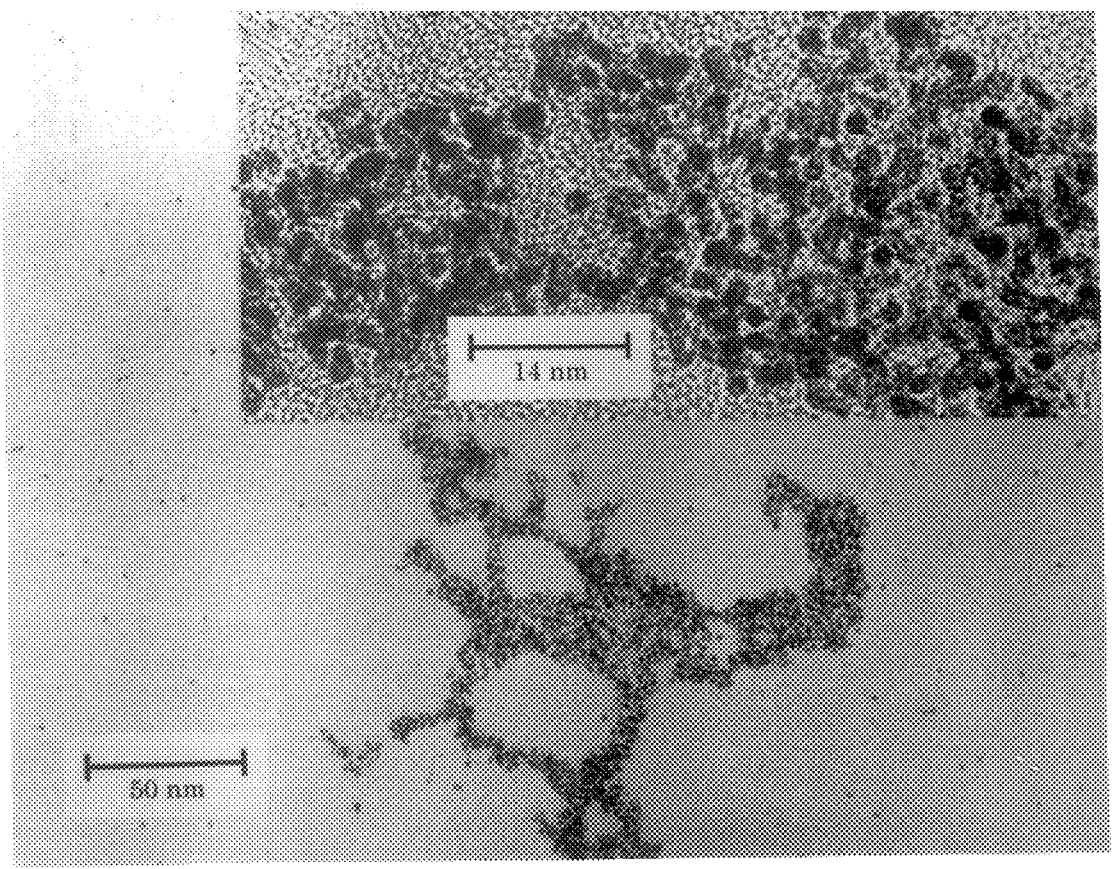
FIG. 2 is a HRTEM micrograph of the platinum colloid of Example 3 at a magnification of 200,000 (insert 700,000).

Under argon, 50 ml of propylene carbonate, 200 mg of platinum dichloride and 235 mg of tetramethylammonium acetate are electrolyzed between two platinum electrodes. The reaction is performed in an ultrasonic bath at a controlled temperature of 25° C. The electrolysis proceeds in a galvanostatic manner at a current density of 3 mA/cm$^2$. After a charge of 3436·10$^{-4}$ Ah has flown, the synthesis is completed, and the deep-brown colloidal solution is filtered over a glass filter frit. The product thus obtained contains platinum particles of between 2 and 3 nm in a narrow size distribution (FIG. 2). By adding diethyl ether, the colloid can be obtained as a slightly smearing solid which can be redispersed in propylene carbonate.

EXAMPLE 4

Preparation of propylene carbonate stabilized rhodium colloid

Figure 3:
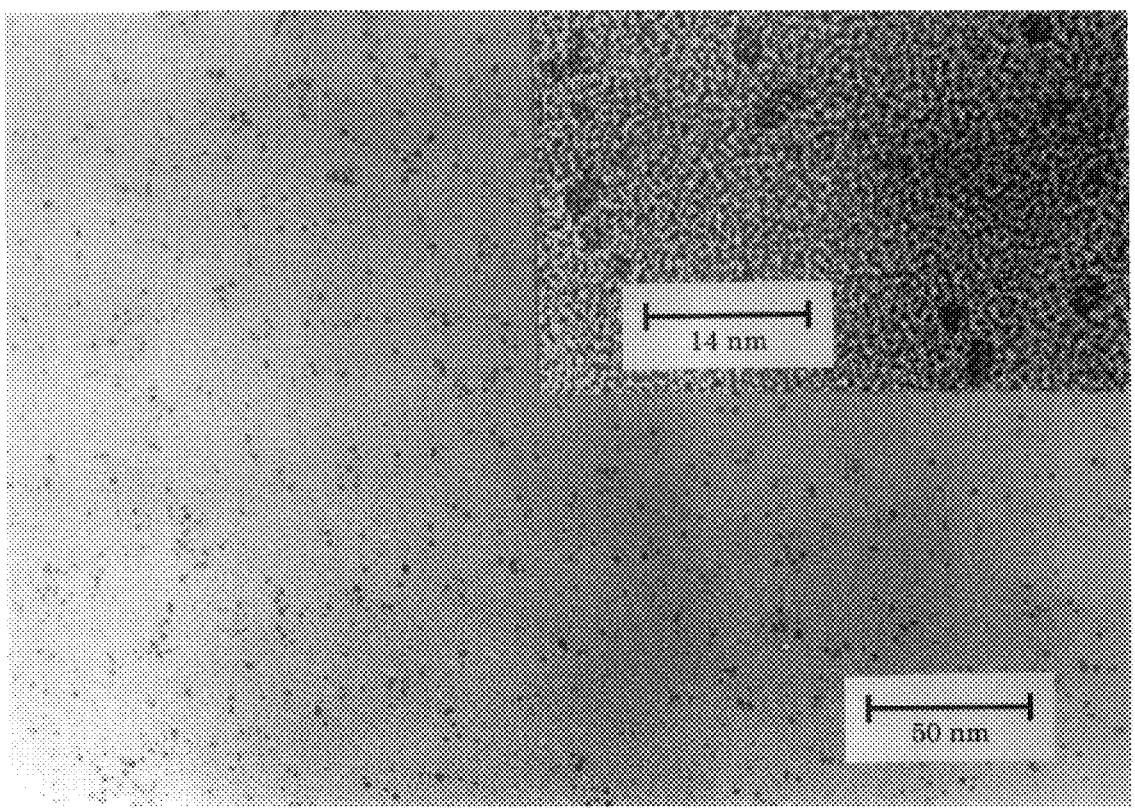
FIG. 3 is a HRTEM micrograph of the rhodium colloid of Example 4 at a magnification of 200,000 (insert 700,000).

Under argon, 50 ml of propylene carbonate, 200 mg of rhodium trichloride and 275 mg of tetramethylammonium acetate are electrolyzed between two platinum electrodes. The reaction is performed in an ultrasonic bath at a controlled temperature of 25° C. The electrolysis proceeds in a galvanostatic manner at a current density of 3 mA/cm$^2$. After a charge of 12,777·10$^{-4}$ Ah has flown, the synthesis is completed, and the deep-brown colloidal solution is filtered over a glass filter frit. The product thus obtained contains rhodium particles of between 2 and 4 nm in a narrow size distribution (FIG. 3). By adding diethyl ether, the colloid can be obtained as a slightly smearing solid which can be redispersed in propylene carbonate.

EXAMPLE 5

Preparation of propylene carbonate stabilized platinum colloid

Figure 4:
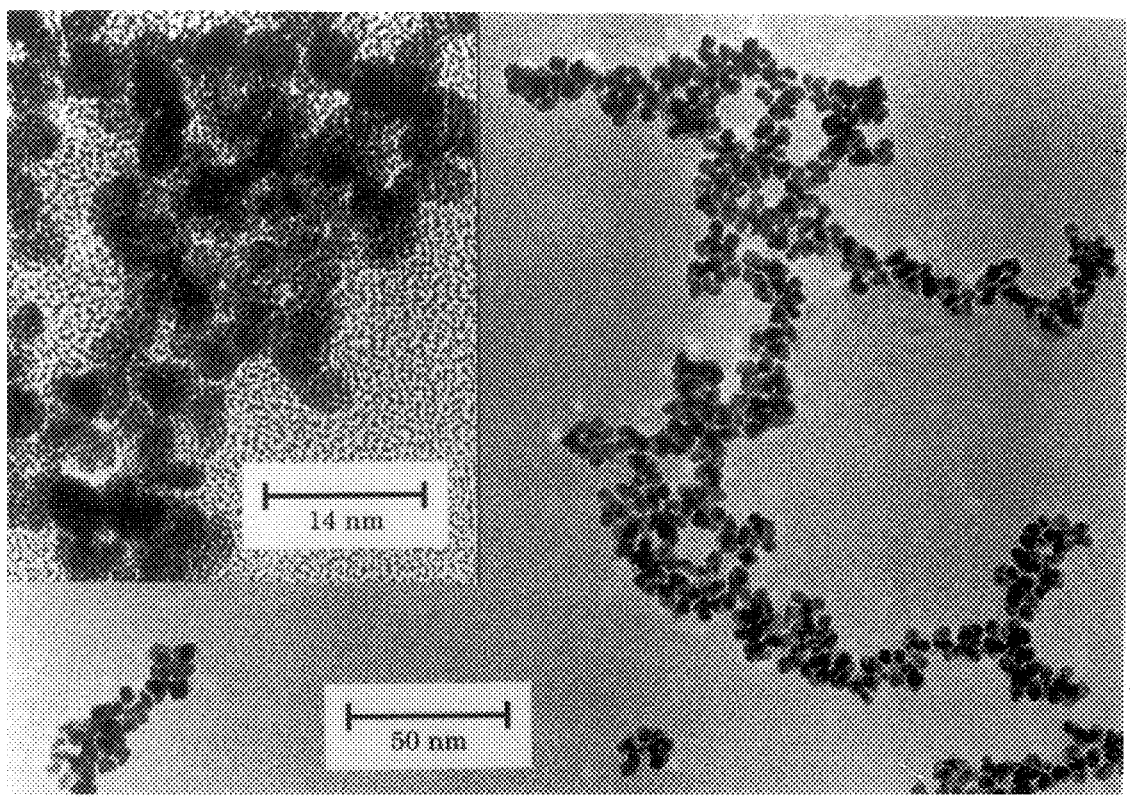
FIG. 4 is a HRTEM micrograph of the platinum colloid of Example 5 at a magnification of 200,000 (insert 700,000).

Under argon, 10 ml of propylene carbonate, 66 mg of platinum dichloride and 1 ml of ethanol are heated at 110° C. for two hours. The reaction is performed in an ultrasonic bath. After the reaction, the product is obtained as a deep-brown colloidal solution which is filtered over a glass filter frit. The size of the platinum particles is between 4 and 6 nm and exhibits a narrow size distribution (FIG. 4).

EXAMPLE 6

Preparation of propylene carbonate stabilized platinum colloid

Under argon, 10 ml of propylene carbonate, 66 mg of platinum dichloride and 1 ml of methanol are heated at 110° C. for two hours. The reaction is performed in an ultrasonic bath. After the reaction, the product is obtained as a deep-brown colloidal solution which is filtered over a glass filter frit. The size of the platinum particles is within a range of 7 and 8 nm.

EXAMPLE 7

Preparation of propylene carbonate stabilized platinum colloid

Under argon, 10 ml of propylene carbonate, 66 mg of platinum dichloride and 1 ml of isopropanol are heated at 110° C. for two hours. The reaction is performed in an ultrasonic bath. At the end of the reaction, the product is obtained as a deep-brown colloidal solution which is filtered over a glass filter frit. The size of the platinum particles is between 2 and 4 nm.

EXAMPLE 8

Preparation of bimetallic copper-palladium colloid

Under argon, 10 ml of propylene carbonate, 1 ml of ethoxyethanol, 113 mg of palladium acetate and 91 mg of copper acetate are heated at 110° C. for two hours. The reaction is performed in an ultrasonic bath. After the reaction, the product is obtained as a deep-brown colloidal solution which is filtered over a glass filter frit.

EXAMPLE 9

Preparation of stilbene (3.5 mole percent catalyst)

Under argon, a solution containing 122 mg of chlorobenzene, 229 mg of sodium carbonate, 141 mg of styrene and 1 ml of propylene carbonate stabilized colloid solution with a palladium content of 4.023 mg is heated at 155° C. with stirring in a sealed vessel for 65 h. At the end of the reaction, 2 ml of diethyl ether is added, and the mixture is filtered. The yield of desired product as determined by GC is 34%.

EXAMPLE 10

Preparation of p-nitrostilbene

Under argon, a solution containing 218 mg of p-nitrobromobenzene, 141 mg of styrene, 0.3 ml of triethylamine, and 1 ml of propylene carbonate stabilized colloid solution with a palladium content of 4.023 mg is heated at 130° C. with stirring in a sealed vessel for 4.5 h. At the end of the reaction, 2 ml of diethyl ether/ dichloromethane (1:1) is added, and the mixture is filtered. The yield of desired product as determined by GC is 96%.

EXAMPLE 11

Preparation of p-acetostilbene

Under argon, a solution containing 215 mg of p-acetobromobenzene, 141 mg of styrene, 0.3 ml of triethylamine, and 1 ml of propylene carbonate stabilized colloid solution with a palladium content of 4.023 mg is heated at 130° C. with stirring in a sealed vessel for 21 h. After the end of the reaction, 2 ml of diethyl ether/dichloromethane (1:1) is added, and the mixture is filtered. The yield of desired product as determined by GC is 56%.

EXAMPLE 12

Thermal stability

The thermal stability of propylene carbonate stabilized palladium colloids as compared to that of $R_4N^+X^-$ palladium colloids can be determined as follows. A palladium colloid obtained according to the above Examples (size 8–10 nm) is heated at 150–160° C. for three days. There is neither precipitation of palladium powder nor any optical change.

In contrast, if a tetrahydrofurane solution of tetraoctylammonium bromide stabilized palladium clusters (size 7–9 nm) is heated at 130–140° C. in a sealed vessel for three hours, large amounts of insoluble palladium powder are formed.

EXAMPLE 13

Preparation of stilbene (1 mole percent catalyst)

Under argon, a solution containing 122 mg of chlorobenzene, 106 mg of sodium carbonate, 157 mg of styrene and 1 ml of propylene carbonate stabilized 0.001 M colloid solution is heated at 155° C. with stirring in a sealed vessel for 17 h. At the end of the reaction, 2 ml of diethyl ether is added, and the mixture is filtered. The yield of isolated trans-stilbene is 15%.

What is claimed is:

1. A size-selective electrochemical process for preparing soluble transition metal colloids or bimetallic colloids, said metal colloids or bimetallic colloids being stabilized by solvents exclusively and having particle sizes ranging from 1 to 15 nm, said process comprising electrochemically reducing transition metal salts in the presence of a polar stabilizing solvent to form said metal colloids or bimetallic colloids.

2. The process according to claim 1, wherein said transition metal salts are electrochemically reduced at the cathode.

3. The process according to claim 2, wherein said transition metal salts are generated by electrochemical dissolution of a metal sacrificial anode.

4. The process according to claim 2, wherein two different metal salts are reduced at the cathode to form bimetallic colloids.

5. The process according to claim 4, wherein one of the two metal salts is generated by dissolution of a metal sacrificial anode.

6. The process according to claim 2, wherein different particle size distributions are obtained by utilizing different conducting salts.

7. The process according to claim 1, characterized by utilizing metals of groups IIIb, IVb, Vb, VIIb, VIII, Ib, IIb, IIIa, IVa or Va of the Periodic Table.

8. The process according to claim 1, characterized in that organic carbonates or urea derivatives are utilized as the polar solvent serving as a colloid stabilizer in the preparation of the metal colloid.

9. A process for the fixing of preformed metal clusters to supports, comprising coating solvent-stabilized metal colloids prepared according to claim 1 onto solid supports to form shell catalysts.

10. A process for the catalytic formation of C—C bonds, comprising conducting a Heck reaction in the presence of a catalyst, said catalyst comprising solvent-stabilized Pd colloids prepared according to claim 1.

11. A size-selective process for preparing soluble transition metal colloids or bimetallic colloids, said metal colloids or bimetallic colloids being stabilized by solvents exclusively and having particle sizes ranging from 1 to 15 nm, said process comprising reducing transition metal salts by heating said transition metal salts in the presence of a polar stabilizing solvent and an alcohol as a reductant to form said metal colloids or bimetallic colloids.

12. The process according to claim 11, wherein different particle size distributions are obtained by utilizing different alcohols as reductants.

13. The process according to claim 11, characterized by utilizing metals of groups IIIb, IVb, Vb, VIIb, VIII, Ib, IIb, IIIa, IVa or Va of the Periodic Table.

14. The process according to claim 11, characterized in that organic carbonates or urea derivatives are utilized as the polar solvent serving as a colloid stabilizer in the preparation of the metal colloid.

15. A process for the fixing of preformed metal clusters to supports, comprising coating solvent-stabilized metal colloids prepared according to claim 11 onto solid supports to form shell catalysts.

16. A process for the catalytic formation of C—C bonds, comprising conducting a Heck reaction in the presence of a catalyst, said catalyst comprising solvent-stabilized Pd colloids prepared according to claim 11.

* * * * *